United States Patent [19]

Lorenz et al.

[11] 4,260,768

[45] Apr. 7, 1981

[54] COPOLYMERIZABLE, ULTRAVIOLET LIGHT ABSORBER 2-(2H-BENZOTRIAZOL-2-YL)-4-ALKYL-PHENOL ACRYLIC ACID ESTERS

[75] Inventors: Donald H. Lorenz, Basking Ridge, N.J.; Bruce A. Gruber, Worthington, Ohio

[73] Assignee: GAF Corporation, New York, N.Y.

[21] Appl. No.: 112,881

[22] Filed: Jan. 17, 1980

[51] Int. Cl.$^3$ .......................................... C07D 249/20
[52] U.S. Cl. ..................... 548/261; 424/59; 526/259
[58] Field of Search ........................................ 548/261

[56] References Cited

U.S. PATENT DOCUMENTS 3,159,646 12/1964 Millionis et al. ............... 548/261
3,936,418 2/1976 Pond et al. .................... 548/261

Primary Examiner—Paul M. Coughlan, Jr.
Attorney, Agent, or Firm—James Magee, Jr.; Walter Katz

[57] ABSTRACT

This invention relates to copolymerizable ultraviolet light absorber compounds having the formula:

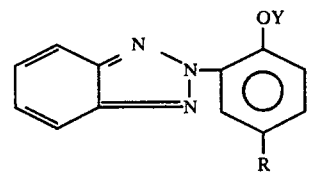

where
R is hydrogen or alkyl $C_1$–$C_6$; and
Y is a copolymerizable radical selected from acrylyl, acryloxyalkyl, acryloxyhydroxyalkyl, and alkylacryloxyhydroxyalkyl.

7 Claims, No Drawings

COPOLYMERIZABLE, ULTRAVIOLET LIGHT ABSORBER 2-(2H-BENZOTRIAZOL-2-YL)-4-ALKYLPHENOL ACRYLIC ACID ESTERS

BACKGROUND OF THE INVENTION

1. Field of the Invention

This invention relates to novel copolymerizable ultraviolet light absorber compounds, and, more particularly, to 2-(2H-benzotriazol-2-yl)-4-alkylphenol acrylic acid ester compounds which are copolymerizable with vinyl monomers to provide polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,724. These ultra-violet absorbers are mechanically mixed with the plastic materials to prevent discoloration and degradation of the material. However, it has been observed that such absorbers sometimes fail or are blocked out of the plastic under adverse weather conditions before the lifetime of the protected material. Also, it is not possible to use all of these ultra-violet absorbers with radiation curing of the plastic material. Another disadvantage of these ultra-violet absorbers is the high amount of absorber needed for protection of some materials.

Accordingly, it is an object of the present invention to provide novel copolymerizable ultraviolet light absorber compounds which are substantially free of the disadvantages of the prior art.

A particular object of this invention is to provide novel compounds which can be copolymerized directly with monomers, such as plastic material, to provide more permanent ultraviolet light protection.

These and other objects and features of the invention will be made apparent from the following more particular description of the invention.

SUMMARY OF THE INVENTION

What is provided herein are improved, novel copolymerizable ultraviolet light absorber compounds of the formula:

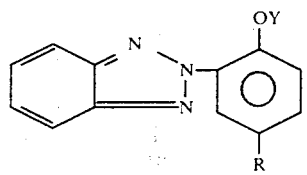

where
R is hydrogen or alkyl $C_1$–$C_6$; and
Y is a copolymerizable radical having 3–12 carbon atoms and selected from acrylyl, alkylacrylyl, acryloxyalkyl, and alkylacryloxyhydroxyalkyl.

In the best mode of the invention, R is methyl and Y is acryloyl.

DETAILED DESCRIPTION OF THE INVENTION

The compounds of the invention contain ultraviolet light absorber and copolymerizable portions in the same molecule. These portions are effectively separated so that each can perform its own function without interference from the other. Therefore, the absorber portion does not inhibit the copolymerization, and the ethylenic radical does not affect the light absorbing properties of the molecule.

The Y radical is copolymerizable with vinyl monomers so that the ultraviolet absorber becomes an integral part of the polymer. Suitable Y groups have 3–12 carbon atoms and are derived from acryloyl, alkylacryloyl, acryloxyalkyl, acryloxyhydroxyalkyl and alkylacryloxyhydroxyalkyl. The preferred groups are acryloyl, methacryloyl, acryloxyhydroxypropyl, and methacryloxyhydroxypropyl. The best mode is represented by acryloyl.

The novel compounds of the invention may be prepared, e.g. from 2-(2H-benzotriazol-2-yl)-4-alkylphenol by esterification with an acryloyl halide. The compounds herein are yellow solids which are insoluble in water. The benzotriazol-2-yl chromophore of the compounds herein has ultraviolet absorbence peak at about 290–300 nm, but no visible absorbance.

The flow sheet below illustrates the reaction for preparing the compounds of the invention.

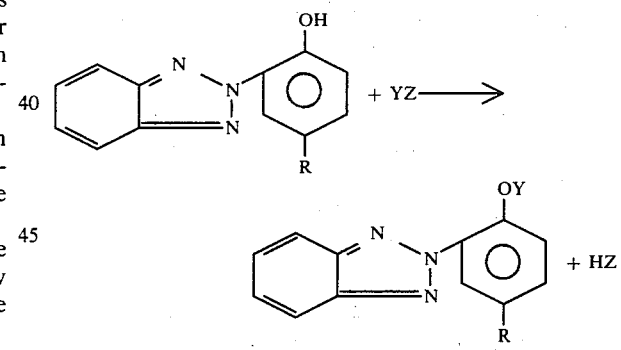

where Z is a halide and R and Y are as defined above.
Representative Y groups are

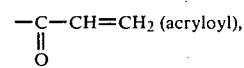

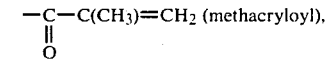

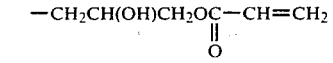

(3-acryloxy-2-hydroxypropyl), and

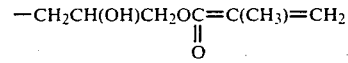

(3-methacryloxy-2-hydroxypropyl).

The esterification step is carried out by reaction of the phenol in a suitable solvent such as acetone, with a reactive acryloyl compound, such as an acryloyl halide, e.g. acryloyl chloride or acryloyl bromide, in aqueous base, such as a sodium hydroxide solution, at room temperature. Suitably the molar ratios of the reactants are controlled to provide at least 1:1 molar ratio of the acryloyl halide to the phenol starting material. The product of the reaction is precipitated, filtered, and dried. The yield of the product in the esterification is about 70%.

The compounds of the invention may be copolymerized with monomers and oligomers by conventional free radical or with radiation curing, to provide useful polymeric coatings, or formulated into cosmetic preparations, such as skin and hair care products.

The following examples will describe the invention with more particularity.

EXAMPLE 1

4-Methyl-2-(2H-Benzotriazol-2-Yl)Phenyl Acrylate

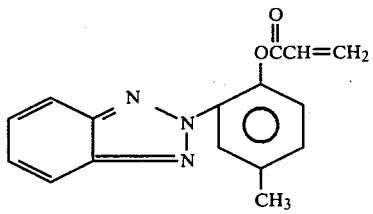

Into a flask provided with a magnetic stirrer is added 10.0 g of 2-(2H-benzotriazol-2-yl)-4-methylphenol dissolved in 350 ml acetone. Then 10% NaOH is added dropwise until the pH is 9. With stirring, 4.1 g of acryloyl chloride is added dropwise while maintaining the pH between 7 and 9 by addition of dilute base. After the addition is complete, the solvent is evaporated leaving a yellow residue which is dissolved in 80 ml ether and extracted with an equal volume of 5% NaOH solution until the aqueous washings are colorless. After evaporation of the ether, there is left 8.4 g of a yellow residue as the product, whose structure, is confirmed by NMR. The yield is 67.7%.

EXAMPLE 2

Copolymerization with Styrene

Into a 3-necked flask, equipped with a magnetic stirrer, thermometer heating mantle, N₂ purge apparatus and a reflux condenser is charged 50 g of styrene, 0.75 g of the UV absorber, namely, the compound of Example 1, and 69 ml of toluene. While stirring and with a nitrogen purge, the contents then are heated to 109° C. and 0.25 of benzoyl peroxide in 6 ml of toluene is added. The polymerization is continued for 17 hours. A polymer is recovered; analysis of the polymer indicates an incorporation of the UV absorber into the polymer structure.

EXAMPLE 3

4-Methyl-2-(2H-Benzotriazol-2-Yl)Phenyl Methacrylate

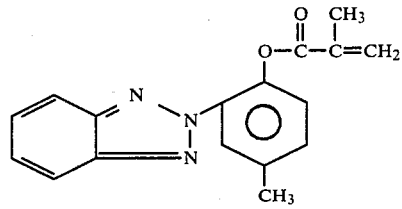

Using an equivalent amount of methacryloyl chloride in place of acryloyl chloride in Example 1, the desired methacrylate compound is obtained in comparable yield.

EXAMPLE 4

3-[4-Methyl-2-(2H-Benzotriazol-2-Yl]-3-Phenoxy-2-Hydroxypropyl Acrylate

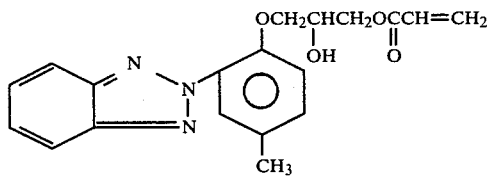

The procedure of Example 1 is followed except that the phenol, glycidyl acrylate and tetramethylammonium chloride are heated at 70°–90° C. for 5 hrs., and excess glycidal acrylate removed by vacuum distillation, to provide the desired compound.

EXAMPLE 5

3-[4-Methyl-2-(2H-Benzotriazol-2-Yl)]-3-Phenoxy-2-Hydroxypropyl Methacrylate

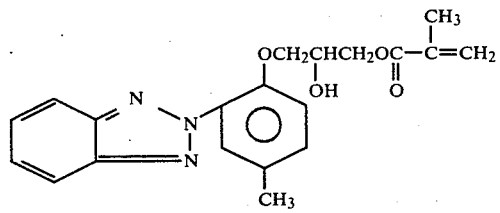

Using glycidyl methacrylate in place of glycidyl acrylate in Example 4 gives the corresponding methacrylate compound.

EXAMPLE 6

The monomer compound of Example 1 is copolymerized with another monomer by charging a flask with 150 ml ethanol, 1.5 g 4-methyl-2-(2H-benzotriazol-2-yl)-phenoxy acrylate and 50 g vinyl pyrrolidone. The contents are heated to 75° C. under N₂ and polymerization is initiated with 0.2 g azobisisobutyronitrile (AIBN). After 1.5 hrs., another 0.2 g AIBN is added and heating is continued for another 1.5 hrs. The solvent is concentrated and added to stirred ether. A white precipitate of the copolymer is obtained which is filtered and dried, giving 18 g (36%) of product. A 5% aqueous solution of the copolymer is filtered; the ultraviolet spectra of the filtrate shows that the copolymer contains 5.8% of the absorber compound.

While certain preferred embodiments of the present invention have been illustrated by way of specific example it is to be understood that the present invention is in no way to be deemed as limited thereto but should be construed as broadly as all or any equivalents thereof.

What is claimed is:

1. Ultraviolet light absorber compounds having the formula

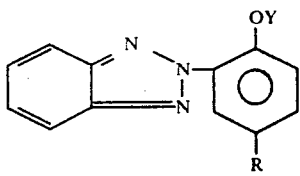

where R is hydrogen or alkyl $C_1$–$C_6$; and

Y is a radical 3–12 carbon atoms and selected from the group consisting of acrylyl, methacrylyl, acryloxyalkyl and alkylacryloxyhydroxyalkyl.

2. Compounds according to claim 1 wherein R is methyl.

3. Compounds according to claim 1 in which Y is acrylyl, methacrylyl, 3-acryloxy-2-hydroxypropyl or 3-methacryloxy-2-hydroxypropyl.

4. A compound according to claim 1 which is 4-methyl-2-(2H-benzotriazol-2-yl)-phenyl acrylate.

5. A compound according to claim 1 which is 4-methyl-2-(2H-benzotriazol-2-yl)-phenyl methacrylate.

6. A compound according to claim 1 which is 3-[4-methyl-2-(2H-benzotriazol-2-yl)]-3-phenoxy-2-hydroxypropyl acrylate.

7. A compound according to claim 1 which is 3-[4-methyl-2-(2H-benzotriazol-2-yl)]-3-phenoxy-2-hydroxypropyl methacrylate.

* * * * *